(12) United States Patent
Park

(10) Patent No.: US 12,220,307 B2
(45) Date of Patent: Feb. 11, 2025

(54) PASSIVELY-COUPLED EYE IMPLANT

(71) Applicant: Joon Bu Park, Las Vegas, NV (US)

(72) Inventor: Joon Bu Park, Las Vegas, NV (US)

( * ) Notice: Subject to any disclaimer, the term of this patent is extended or adjusted under 35 U.S.C. 154(b) by 317 days.

(21) Appl. No.: 17/868,127

(22) Filed: Jul. 19, 2022

(65) Prior Publication Data

US 2024/0024091 A1 Jan. 25, 2024

(51) Int. Cl.
*A61F 2/14* (2006.01)
*A61N 1/05* (2006.01)

(52) U.S. Cl.
CPC .............. *A61F 2/14* (2013.01); *A61N 1/0543* (2013.01)

(58) Field of Classification Search
CPC .................................................. A61N 1/0543
See application file for complete search history.

(56) References Cited

U.S. PATENT DOCUMENTS

| | | | |
|---|---|---|---|
| 5,935,155 | A | 8/1999 | Humayun et al. |
| 9,030,079 | B1 | 5/2015 | Roberts et al. |
| 2004/0098067 | A1* | 5/2004 | Ohta ..................... A61F 9/08 607/54 |
| 2008/0288067 | A1 | 11/2008 | Flood |
| 2010/0204754 | A1 | 8/2010 | Gross et al. |
| 2017/0232251 | A1 | 8/2017 | Neysmith et al. |
| 2017/0368351 | A1* | 12/2017 | Liran .................... A61N 1/3787 |

OTHER PUBLICATIONS

Beauchamp et al., "Dynamic Electrical Stimulation of Sites in Visual Cortex Produces Form Vision in Sighted and Blind Humans," BioRXiv, Nov. 2018, 24 pages.
Dobelle et al., "Artificial Vision for the Blind: Electrical Stimulation of Visual Cortex Offers Hope for a Functional Prosthesis," Science, Feb. 1974, 183(4123):400-444.
Dobelle, "Artificial Vision for the Blind by Connecting a Television Camera to the Visual Cortex," ASAIO Journal, Jan. 2000, 46(1):3-9.
Fink et al., "Microcomputer-based Artificial Vision Support System for Real-Time Image Processing for Camera-Drive Visual Prostheses," Journal of Biomedical Optics, Jan. 2010, 15(1):1-10.
Finn et al., "Argus II Retinal Prosthesis System: A Review of Patient Selection Criteria, Surgical Considerations, and Post-Operative Outcomes," Clinical Ophthalmology, Jun. 2018, 12(2018):1089-1097.
Hussain et al., "NIR self-powered photodetection and gate tunable rectification behavior in 2D GeSe/MoSe2 heterojunction diode," Scientific Reports, Feb. 2021, 11(1):1-8.
Lee et al., "Self-Powered Sensors: New Opportunities and Challenges from Two-Dimensional Nanomaterials," Molecules, Aug. 2021, 26(16), 24 pages.

(Continued)

*Primary Examiner* — Javier G Blanco
(74) *Attorney, Agent, or Firm* — Fish & Richardson P.C.

(57) ABSTRACT

An eye implant includes a plurality of photodetectors and a plurality of electrodes electrically coupled to the plurality of photodetectors. The plurality of electrodes are configured to electrically couple each photodetector of the plurality of photodetectors to one or more neurons, and the electrical coupling between each photodetector and the one or more neurons is entirely passive.

11 Claims, 9 Drawing Sheets

(56) References Cited

OTHER PUBLICATIONS

Lin et al., "High-Performance Self-powered Photodetectors Based on ZnO/ZnS Core-Shell Nanorod Arrays," Nanoscale Research Letters, Dec. 2016, 11(1):1-7.
Mirochnik et al., "Contemporary Approach to Visual Prostheses," Military Medical Research, Dec. 2019, 6(1):1-9.
Park et al., "Biomaterials; An Introduction," 3rd ed., Jul. 2007, Figures 11-28, p. 314, 1 page.
Qiao et al., "Self-Powered Photodetectors Based on 2D Materials," Advanced Optical Materials, Sep. 2019, 8(1), 20 pages.
Stingl et al., "Subretinal Visual Implant Alpha IMS—Clinical Trial Interim Report," Vision Research, Jun. 2015, 111(2015):149-160.
Yang et al., "Mechanism, Material, Design, and Implementation Principle of Two-Dimensional Material Photodetectors," Oct. 2021, Nanomaterials, 11(10), 34 pages.
International Search Report and Written Opinion in International Appln. No. PCT/US2023/27086, mailed on Oct. 13, 2023, 15 pages.

\* cited by examiner

PASSIVELY-COUPLED EYE IMPLANT

FIELD OF THE DISCLOSURE

Technologies are described related to eye implants for vision restoration.

BACKGROUND

A visual prosthesis is an experimental visual device intended to restore functional vision in those suffering from partial or total blindness. In some visual prostheses, a computational layer between a sensing component (e.g., a camera) and the human body (optic nerves) performs processing to structure image data in a format interpretable by the human body.

SUMMARY

Some aspects of this disclosure describe an eye implant. The eye implant includes a plurality of photodetectors and a plurality of electrodes electrically coupled to the plurality of photodetectors. The plurality of electrodes are configured to electrically couple each photodetector of the plurality of photodetectors to one or more neurons, and the electrical coupling between each photodetector and the one or more neurons is entirely passive.

This and other described devices, such as eye implants and portions thereof, can have any one or more of at least the following characteristics.

In some implementations, the plurality of photodetectors include photodiodes.

In some implementations, the plurality of electrodes are configured such that the one or more neurons electrically coupled to each photodetector are electrically disconnected from each other photodetector of the plurality of photodetectors.

In some implementations, the electrical coupling between each photodetector and the one or more neurons is free from digital signal processing.

In some implementations, the plurality of photodetectors are arranged in a photodetector array.

In some implementations, the plurality of electrodes are arranged in an electrode array, each photodetector of the photodetector array is electrically coupled to a corresponding electrode of the electrode array, and the electrodes of the electrode array are arranged in an array pattern that matches an array pattern in which the photodetectors of the photodetector array are arranged.

In some implementations, the eye implant includes passive circuitry electrically coupled to a first electrode of the plurality of electrodes. The passive circuitry is configured to adjust a spectral characteristic of a signal sent from a first photodetector of the plurality of photodetectors, through the first electrode, and to the one or more neurons electrically coupled to the first electrode.

In some implementations, the passive circuitry includes a frequency filter.

In some implementations, the passive circuitry is electrically coupled between the first photodetector and the first electrode.

In some implementations, the plurality of photodetectors include self-powered thin-film heterojunction photodetectors.

In some implementations, the self-powered thin-film heterojunction photodetectors include a two-dimensional material.

In some implementations, the plurality of electrodes each include a negative Poisson's ratio material.

In some implementations, for each electrode of the plurality of electrodes, the negative Poisson's ratio material of the electrode is coated by a positive Poisson's ratio material.

In some implementations, the plurality of electrodes include a coating including at least one of a biocompatible polymer or a biocompatible ceramic.

In some implementations, the plurality of electrodes each include an extending tip having a surface, wherein at least a portion of the surface is electrically conductive.

In some implementations, the eye implant includes a substrate having a first surface and a second surface opposite the first surface. The plurality of photodetectors are disposed on the first surface, and the extending tip of each electrode of the plurality of electrodes extends from the second surface away from the substrate.

Details of one or more implementations of the disclosed technologies are set forth in the accompanying drawings and the description below. Other features, aspects, descriptions and potential advantages will become apparent from the description, the drawings and the claims.

Figure 1A:
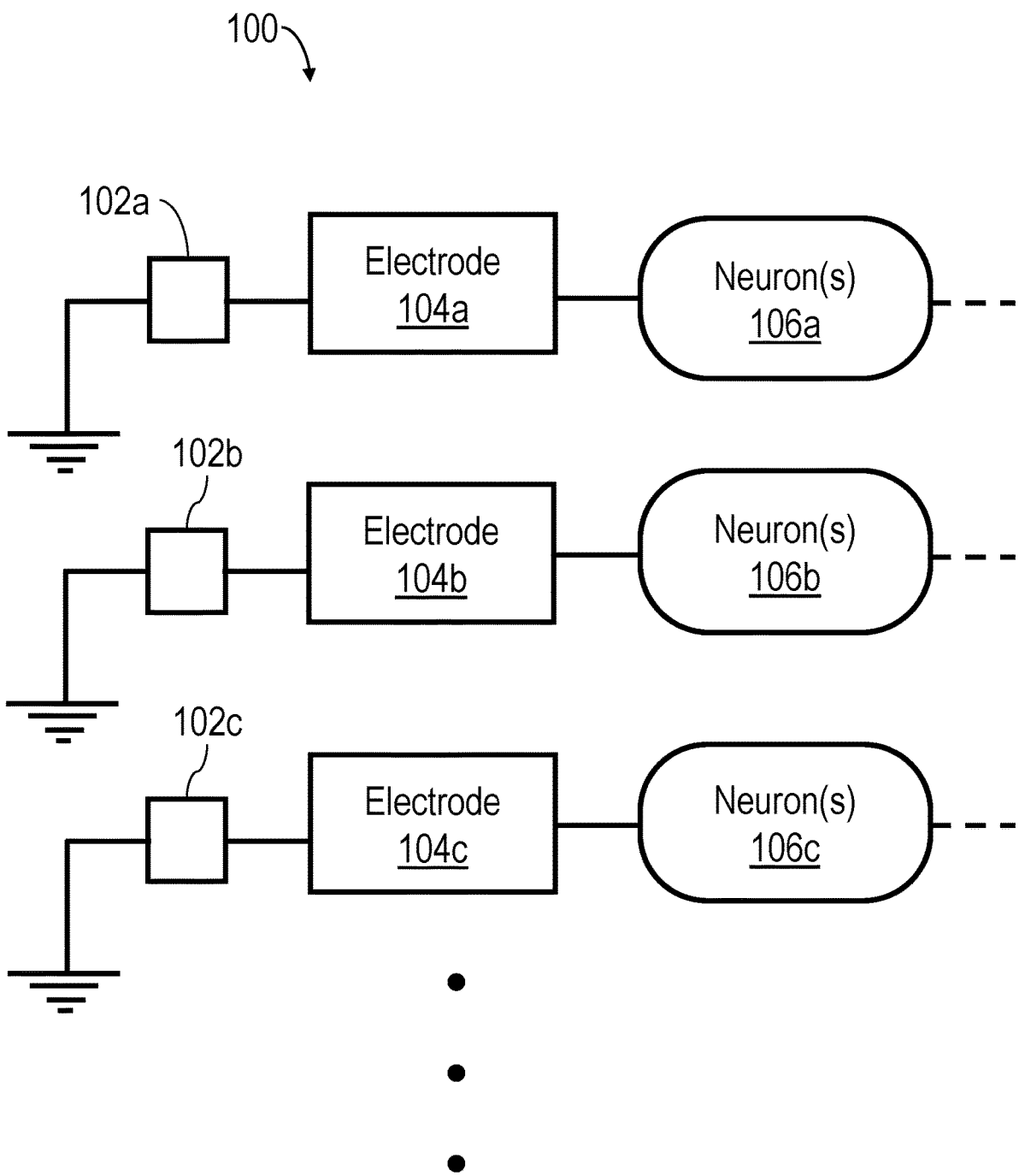
FIGS. 1A-1B are diagrams illustrating couplings in example eye implants.

Certain illustrative aspects of the disclosed technologies are described herein in connection with the following description and the accompanying figures. These aspects are, however, indicative of but a few of the various ways in which the principles of the disclosed technologies may be employed and the disclosed technologies are intended to include all such aspects and their equivalents. Other advantages and novel features of the disclosed technologies may become apparent from the following detailed description when considered in conjunction with the figures.

DETAILED DESCRIPTION

Visual prostheses interface with the human body to provide visual input that would otherwise be provided by a portion of the eye. In a healthy eye, light striking the retina initiates a bio-electrical response that causes neural impulses to be transmitted to the optic nerve. Therefore, an objective of some visual prostheses is to provide electrical signals to the optic nerve, or another type of nerve cell (neuron), to replicate these neural impulses. For example, a camera mounted in the eye or elsewhere on a person's body can capture images that are processed by a powered computing element. The computing element can encode the images into electrical signals that are predicted to be readily interpretable by the optic nerve or another portion of the eye that receives the signals, such as ganglion cells of the retina. The format of these signals, provided by the encoding by the computing element, is determined based on numerous studies that have examined eye and nerve operations, such as nerve action potentials and spatial encoding by the retina.

However, computer processing of the signals relies on constant power consumption, which can impose limits on visual prosthesis operation. When prosthesis operation is reliant on such processing, a battery failure or battery depletion can cause sight to be entirely cut off. Moreover, computer processing may introduce additional failure points into visual prosthesis operation, such as software bugs, reduction in device interoperability over time (e.g., difficulties in connecting an old visual prosthesis to new computer devices to update the software of the visual prosthesis), data bandwidth limitations that may reduce an amount of image data that can be processed in real-time and/or provided in real-time to the human body, and increased prosthesis fragility due to the inclusion of computer components and their interconnections. Other active signal-processing functions may also be associated with some or all of these failure points.

These approaches overlook the fundamental plasticity of nervous system operation. In sighted people, signals from the retina are not subject to digital processing. Rather, the nervous system itself performs whatever signal processing is necessary for vision. Moreover, the nervous system is adaptable over time, as evidenced by studies of subjects wearing "upside down goggles," or "invertoscopes."

Some aspects of this disclosure describe eye implants in which the electrical coupling between photodetectors and neurons, including any signal processing that may be present, is entirely passive. Such implants need not include a power source, a computer processor, or other hardware that can add failure points to optical prostheses. In some cases, the passive eye implants described in this disclosure are facilitated by "self-powered" photodetectors that take advantage of thin-film heterojunctions to provide electrical signals in the absence of photodetector biasing.

As shown in FIG. 1, an example of an eye implant 100 includes multiple photodetectors 102a, 102b, 102c (referred to generically as photodetectors 102). Each photodetector 102 is electrically coupled to a corresponding electrode 104a, 104b, 104c (referred to generically as electrodes 104), which is electrically coupled to one or more corresponding neurons 106a, 106b, 106c (referred to generically as neurons 106). When light strikes the photodetectors 102, signals are generated that are passed through the electrodes 104 to the neurons 106. In some implementations, as discussed in further detail with respect to FIGS. 4A-4C, the signal is processed by one or more passive circuit components.

The photodetectors 102 can include one or more types of photodetector that generate an electrical signal (e.g., current or voltage) in response to illumination. For example, in some implementations, the photodetectors 102 include photodiodes, such as p-n photodiodes, p-i-n photodiodes, avalanche photodiodes, or Schottky photodiodes. In some implementations, the photodetectors 102 include another type of photodetector, such as a visible light-sensitive quantum well photodetector or a visible light-sensitive quantum dot photodetector.

The photodetectors 102 can be formed of one or more materials suitable for detection of visible light, such as an inorganic semiconductor (e.g., silicon, germanium, gallium arsenide, or indium gallium arsenide), an organic semiconductor (e.g., poly(3-hexylthiophene) (P3HT) and/or [6,6]-phenyl-C61-butyric acid methyl ester (PCBM)), and/or another material (e.g., a perovskite material or a two-dimensional material) capable of absorbing photons, transporting photocarriers, and/or performing another photoelectric function.

Figure 2A:
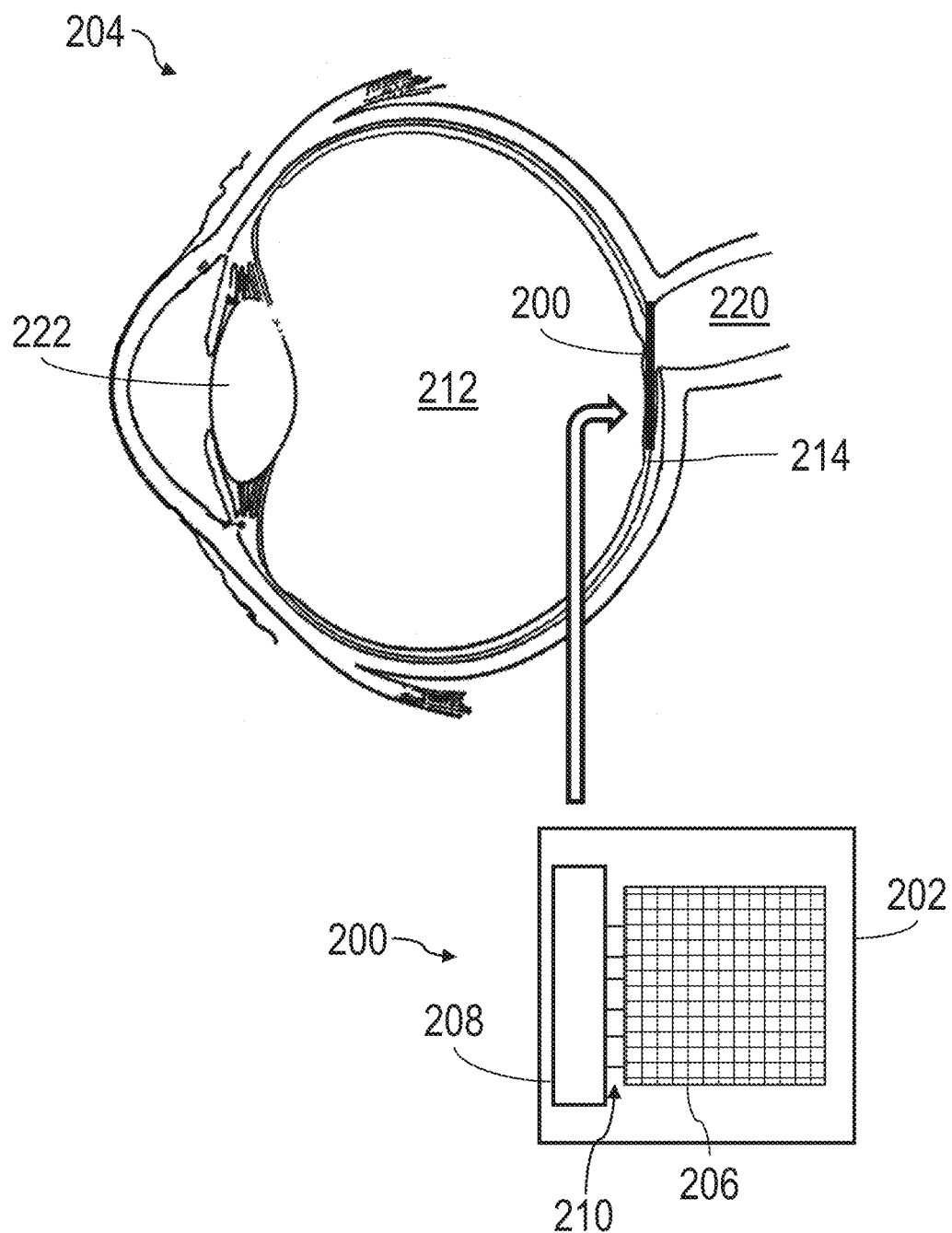
FIGS. 2A-2B are diagrams illustrating examples of an eye implant and its implantation in an eye.
Figure 2B:
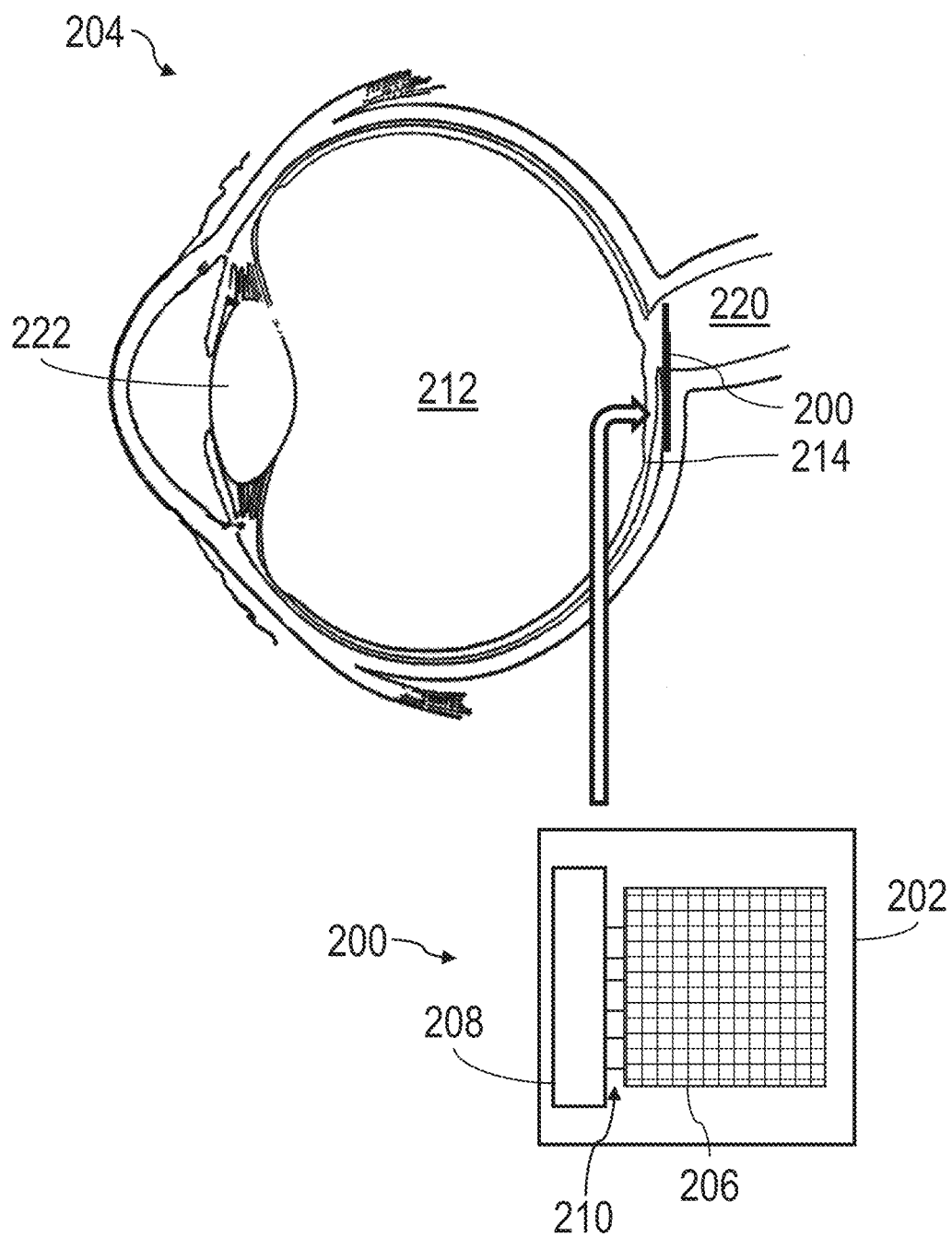

In some implementations, the photodetectors 102 are arranged in an array, e.g., in rows and columns of pixels, each pixel including one or more photodetectors 102. The photodetectors 102 (e.g., the array of photodetectors 102) can be formed on a substrate. For example, as shown in FIGS. 2A-2B, an eye implant 200 includes a substrate 202, such as a semiconductor substrate, a dielectric substrate (e.g., a glass substrate), or a circuit board, such as a printed circuit board (PCB). In some implementations, the substrate 202 or a portion thereof is encapsulated in a biocompatible encapsulant configured to (i) protect components of the eye implant 200 from degradation when the eye implant 200 is implanted in an eye 204 and/or (ii) prevent components of the eye implant 200 from harming the eye 204. For example, the encapsulant can include silicone, a ceramic (e.g., aluminum oxide), a biocompatible polymer, or another suitable material.

Disposed on the substrate 202 is a photodetector array 206 (including photodetectors, such as photodetectors 102, arranged in rows and columns) and circuitry 208 electrically coupled to the photodetector array 206, e.g., by interconnects 210. The photodetector array 206 is optically exposed so as to detect light incident on the photodetector array 206. In some implementations, the photodetector array 206 and/or the circuitry 208 are integrated into the substrate 202, e.g., formed of one or more integrated circuits in the substrate 202. In some implementation, the photodetector array 206 and/or the circuitry 208 are attached to the substrate 202, e.g., bonded/soldered to the substrate 202. For example, the photodetector array 206 and the circuitry 208 can be one or more integrated circuits electrically coupled to and attached to bond pads on the substrate 202. The interconnects 210 can be included as part of an integrated circuit that includes the photodetector array 206 and/or the circuitry 208 and/or the interconnects 210 can be included in the substrate 202 itself, e.g., as metal traces in a printed circuit board.

The eye implant 200 is implanted in the eye 204 to supplement or replace light detection functionality of the eye 204. In some implementations, as shown in FIG. 2A, the eye implant is arranged as an epiretinal implant, e.g., is implanted on the retina 214, such as on a ganglion cell layer of the retina 214. For example, the photodetector array 206 can be in contact with vitreous gel 212 of the eye 202. In some implementations, as shown in FIG. 2B the eye implant is arranged as a subretinal implant, e.g., is implanted under the retina 214. Depending on the arrangement of the eye implant and the configuration of the electrodes of the eye implant, the eye implant can be configured to stimulate ganglion cells, bipolar cells, cells of the optic nerve, or another type of neuron.

Figure 1B:
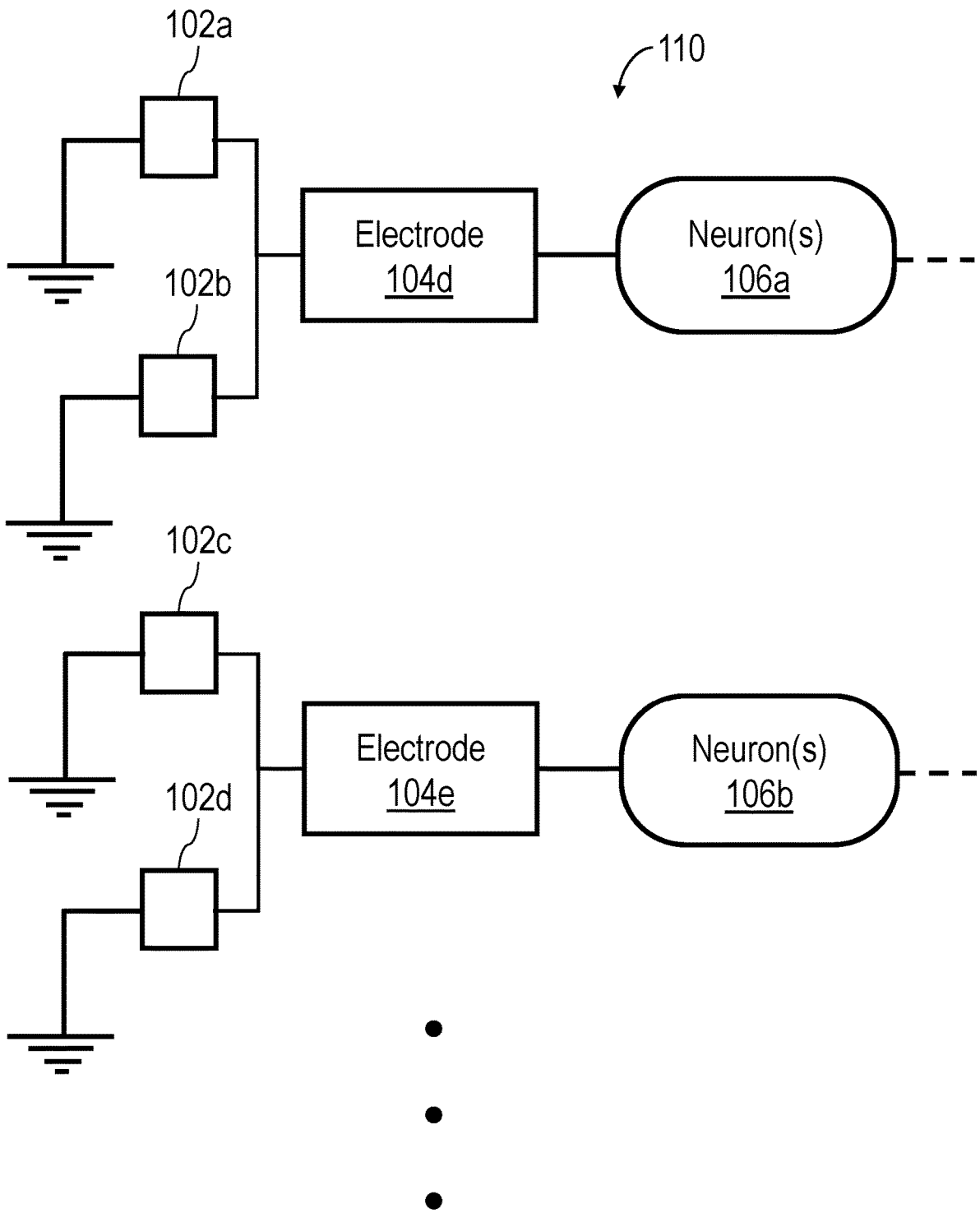

Referring to FIG. 1B, in some implementations, multiple photodetectors are electrically coupled to each electrode. For example, in an example of an eye implant 110, photodetectors 102a and 102b are electrically coupled to electrode 104d, and photodetectors 102c and 102d are electrically coupled to electrode 104e. In some implementations, having multiple photodetectors for each electrode can cause an increased signal magnitude to be transmitted to the neurons 106, e.g., a higher voltage or current, based on the signal being a sum or other combination of multiple signals provided by multiple photodetectors 102.

The electrodes 104 are configured to stimulate the neurons 106 with signals from the photodetectors 102 (in some implementations, processed by additional circuitry) and, accordingly, are electrically coupled to the neurons 106. For example, the electrodes 104 can be directly conductively coupled to neurons 106 (e.g., in contact with the neurons 106) or in close proximity to the neurons 106, such that voltage signals or current signals in the electrodes 104 stimulate the neurons. In some implementations, the electrodes 104 are spaced apart from one another at distances such that each neuron is stimulated by only one electrode 104, e.g., a neuron stimulated by one electrode 104 is electrically disconnected from each other electrode 104.

Figure 3:
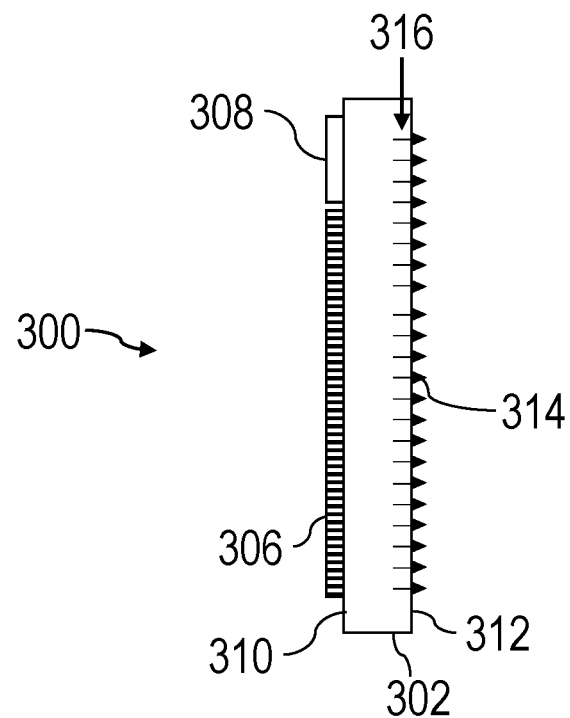
FIG. 3 is a diagram illustrating an eye implant including a substrate.

FIG. 3 illustrates an example configuration of the electrodes 104. In this example, an eye implant 300 includes a substrate 302 (e.g., having characteristics as described for substrate 202), a photodetector array 306 (e.g., having characteristics as described for photodetector array 206), and circuitry 308 (e.g., having characteristics as described for circuitry 208). The photodetector array 306 is disposed on a first surface 310 of the substrate 302, e.g., facing out of the eye in which the eye implant 300 is implanted.

Electrodes 314 are disposed on a second surface 312 that is opposite the first surface 310. The electrodes 314 are arranged to contact the human body, e.g., directly contact neurons or contact portions of the eye in close proximity to neurons. For example, each electrode 314 can stimulate multiple neurons that are in proximity to the electrode 314. In this example, each electrode 314 has an extending tip that extends away from the second surface 312, e.g., in a posterior direction when the eye implant 300 is implanted. In some implementations, the extending tip is sharp, so as to facilitate penetration of the electrodes 314 and effective stimulation of neurons. In some implementations, the extending tip is blunt, e.g., rounded. In some implementations, the electrodes do not include an extending tip, e.g., include pads/bumps arranged to contact the human body. Interconnects 316 (e.g., having characteristics as described for interconnects 210) carry signals from the photodetector array 306, to the circuitry 308, and to the electrodes 314.

In some implementations, the electrodes 314 are coated with one or more biocompatible materials, such as a biocompatible polymer, a biocompatible ceramic, or a biocompatible metal. In some implementations, the biocompatible materials are electrically conducting (e.g., a metal such as PtIr or a ceramic such as TiN), such that portions of the electrodes 314 that would otherwise be exposed are entirely coated in the biocompatible materials. In some implementations, the biocompatible materials are electrically insulating, and a portion of the electrodes 314 is conductive and uncoated.

In some implementations, the electrodes 104 include a material having a negative Poisson's ratio (an "NPR material"). An NPR material is a material that has a Poisson's ratio that is less than zero, such that, when the material experiences a positive strain along one axis (e.g., when the material is stretched), the strain in the material along the two perpendicular axes is also positive (e.g., the material expands in cross-section). Conversely, when the material experiences a negative strain along one axis (e.g., when the material is compressed), the strain in the material along a perpendicular axis is also negative (e.g., the material compresses along the perpendicular axis). By contrast, a material with a positive Poisson's ratio (a "PPR material") has a Poisson's ratio that is greater than zero. When a PPR material experiences a positive strain along one axis (e.g., when the material is stretched), the strain in the material along the two perpendicular axes is negative (e.g., the material compresses in cross-section), and vice versa.

Some NPR materials have a foam structure. An example of an NPR foam structure is a re-entrant structure, which is a foam in which the walls of the cells are concave, e.g., protruding inwards toward the interior of the cells. In a re-entrant foam, compression applied to opposing walls of a cell will cause the other, inwardly directed walls of the cell to buckle inward further, causing the material in cross-section to compress, such that a compression occurs in all directions. Similarly, tension applied to opposing walls of a cell will cause the other, inwardly directed walls of the cell to unfold, causing the material in cross-section to expand, such that expansion occurs in all directions. NPR foams can have a Poisson's ratio of between −1 and 0, e.g., between −0.8 and 0, e.g., −0.8, −0.7, −0.6, −0.5, −0.4, −0.3, −0.2, or −0.1. NPR foams can have an isotropic Poisson's ratio (e.g., Poisson's ratio is the same in all directions) or an anisotropic Poisson's ratio (e.g., Poisson's ratio when the foam is strained in one direction differs from Poisson's ratio when the foam is strained in a different direction).

An NPR foam can be, for example, a polymeric foam, a ceramic foam, a metallic foam, or a combination thereof. Examples of polymeric foams for integration into electrodes of eye implants include thermoplastic polymer foams (e.g., polyester polyurethane or polyether polyurethane); viscoelastic elastomer foams; or thermosetting polymer foams such as silicone rubber. Examples of metallic foams for integration into electrodes of eye implants include metallic foams based on steel (e.g., stainless steel), copper, nickel, aluminum, titanium (e.g., Ti6Al4V, TiNbZr, or unalloyed titanium), or other metals, or alloys thereof. A ceramic foam can be composed of a metal oxide (e.g., aluminum oxide, titanium oxide, or zirconium oxide).

An NPR foam can be polydisperse (e.g., the cells of the foam are not all of the same size) and/or disordered (e.g., the cells of the foam are randomly arranged, as opposed to being arranged in a regular lattice). An NPR foam can have a characteristic dimension (e.g., the size of a representative cell (e.g., average-size cell), such as the width of the cell from one wall to the opposing wall) ranging from 0.005 µm to about 3 mm, e.g., about 0.01 µm, about 0.02 µm, about 0.05 µm, about 0.1 µm, about 0.5 µm, about 1 µm, about 10 µm, about 50 µm, about 100 µm, about 500 µm, about 1 mm, about 2 mm, or about 3 mm, or any range delimited by any two of these values.

In some implementations, the NPR material is an outer material of the electrode, and the NPR material is conductive. For example, the NPR material can be a conductive metallic foam. A conductive outer portion of the electrode, in contact with the human body, facilitates transfer of signals from the electrode to one or more neurons. In some implementations, a bulk material of the electrode is the NPR material.

Figure 6:
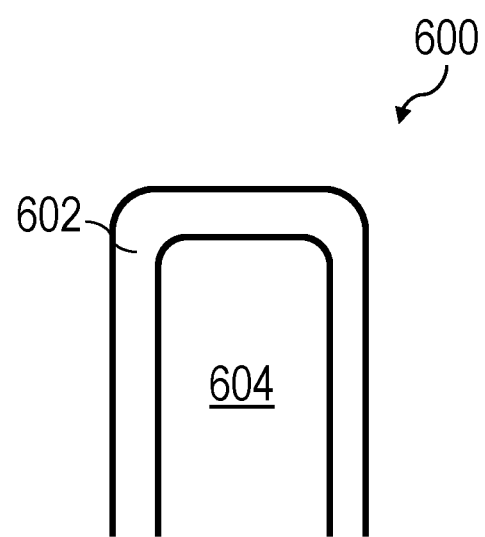
FIG. 6 is a diagram illustrating an example of an electrode including a negative Poisson's ratio material and a positive Poisson's ratio material.

In some implementations, the NPR material is an inner material of the electrode, and an outer material of the electrode is formed from a PPR material. For example, as shown in FIG. 6, an electrode 600 includes an inner NPR portion 604 and an outer PPR portion 602. for example, the PPR portion 602 can be a coating/layer on the NPR portion 604, e.g., deposited on the NPR portion 604 after formation of the NPR portion 604. In some implementations, the inner NPR portion 604 is an insulator, and the outer PPR portion 602 is conductive, e.g., a PPR metal. This can allow the electrode 600 to effectively electrically couple to neuron(s), achieve the mechanical and/or chemical durability and/or biocompatibility provided by PPR materials, and realize the mechanical stability benefits provided by the inclusion of the NPR material of the inner NPR portion 604. For example, in some implementations the outer PPR portion 602 is a biocompatible polymer or a biocompatible ceramic. In some implementations, the PPR material is an inner material of the electrode, and an outer material of the electrode is formed from an NPR material.

Having an NPR material in an electrode of an eye implant can provide advantages in some implementations. The tendency of the NPR material to compress in a traverse direction, rather than expand, in response to compression can reduce stress or strain that may be applied to components of the eye implant and/or portions of the human body in contact with the eye implant, or otherwise help to maintain homeostasis. When an electrode includes both an NPR material and a PPR material, e.g., where one material is inside the other material, the NPR material and the PPR material may respond oppositely to forces, maintaining a more constant total volume of the electrode over time and potentially reducing damage to the electrode and/or harm to the human body.

Referring back to FIG. 3, in some implementations, the electrodes 314 are arranged in an array. For example, in some implementations, each photodetector of the photodetector array 306 is electrically coupled to a corresponding electrode 314, and the electrodes 314 are arranged in an array pattern that matches an array pattern in which the photodetectors are arranged (with the same or different spacing). For example, a first photodetector is adjacent to second and third photodetectors in the photodetector array, the first photodetector is electrically coupled to a first electrode, and the first electrode is adjacent to second and third electrodes in the electrode array, the second and third electrodes coupled to the second and third photodetectors, respectively. Matching patterns may facilitate useful interpretation of provided signals by the nervous system.

Figure 4A:
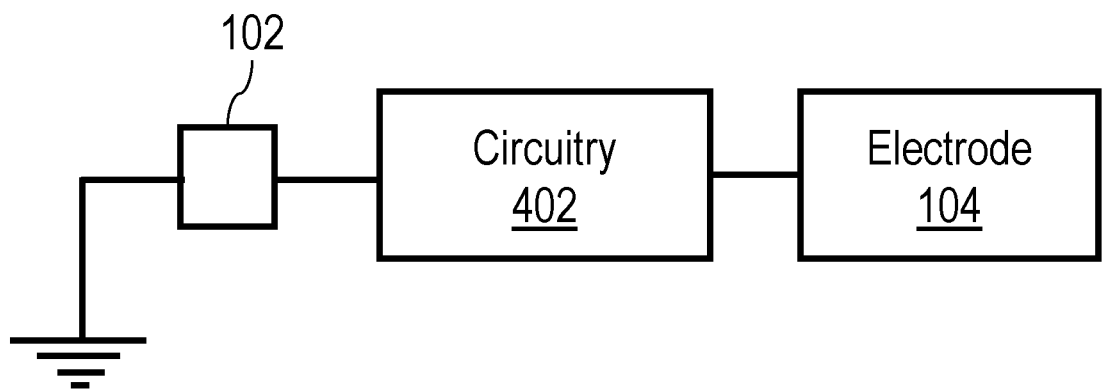
FIGS. 4A-4C are diagrams illustrating examples of circuitry in eye implants.

As described in reference to FIGS. 2-3, in some implementations, the eye implant includes circuitry configured to convert, modify, or otherwise act on signals provided by the photodetectors. As shown in FIG. 4A, circuitry 402 (e.g., circuitry 208 or 308) can be arranged electrically between a photodetector 102 and a corresponding electrode 104. The circuitry 402 is passive, e.g., includes no external power source or powered computation, such as digital signal processing. For example, the circuitry 402 can include one or more resistors, diodes, capacitors, and/or inductors so as to passively modify signals from the photodetector 102.

Figure 4B:
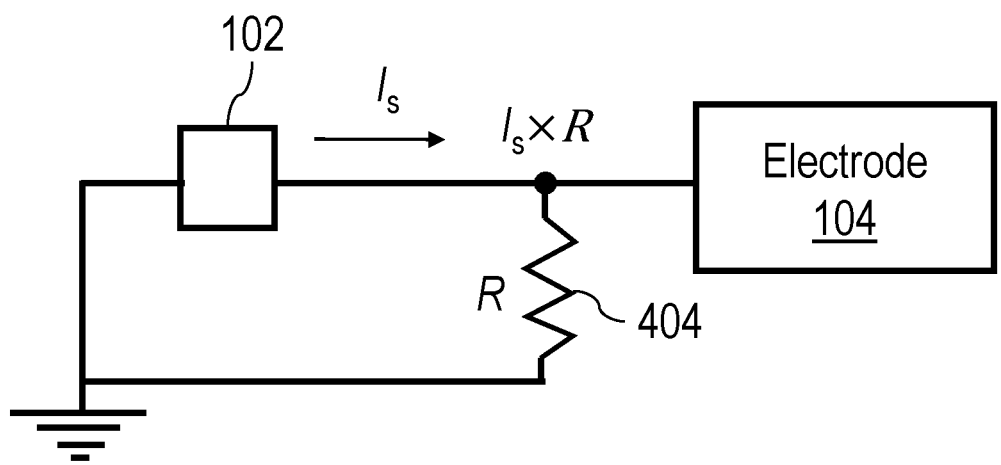

FIG. 4B illustrates an example configuration in which the circuitry 402 includes a resistor 404. The resistor 404 converts a photocurrent $I_S$ generated by the photodetector 102 (based on light detected at the photodetector 102) into a voltage $I_S \times R$, where R is the resistance of the resistor 404. The voltage is provided to the electrode 104, where the voltage can stimulate one or more neurons.

Figure 4C:
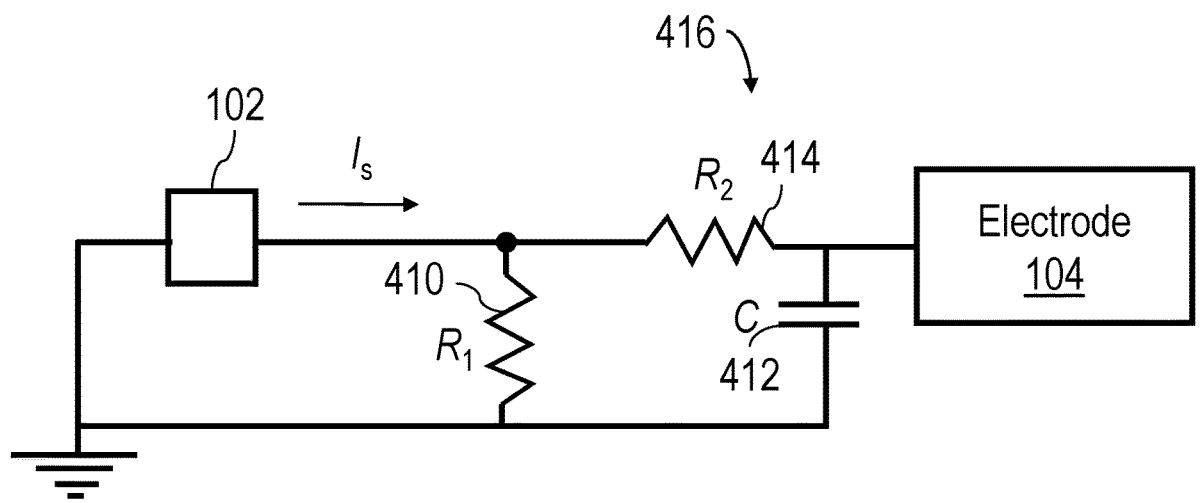

In some implementations, the circuitry 402 is configured to perform passive spectral processing of the signal from the photodetector 102. For example, the circuitry 402 can perform filtering (low-pass, high-pass, band-pass, and/or band-stop filtering), smoothing (e.g., by inclusion of a smoothing capacitor), and/or another operation that modifies frequency characteristic(s) of the signal. For example, as shown in FIG. 4C, the circuitry 402 includes a first resistor 410 that converts the photocurrent $I_S$ into a voltage, and a capacitor 412 and a second resistor 414 that together function as a low-pass filter 416. Accordingly, high-frequency components are removed from the signal provided to the electrode 104. Removal of high-frequency components may improve a reliability of neuron response to stimulation.

In some implementations, the circuitry 402 can provide a self-powered amplifying functionality. For example, even in the absence of a power source, signal combination (e.g., current addition), capacitor-based energy storage followed by discharge, and/or other circuit techniques can allow currents and/or voltages indicative of photodetection to be increased in magnitude for transmission to the electrode and neuron stimulation. In some implementations, the circuitry 402 and any other coupling between the photodetectors and the electrodes includes no amplification.

Figure 5:
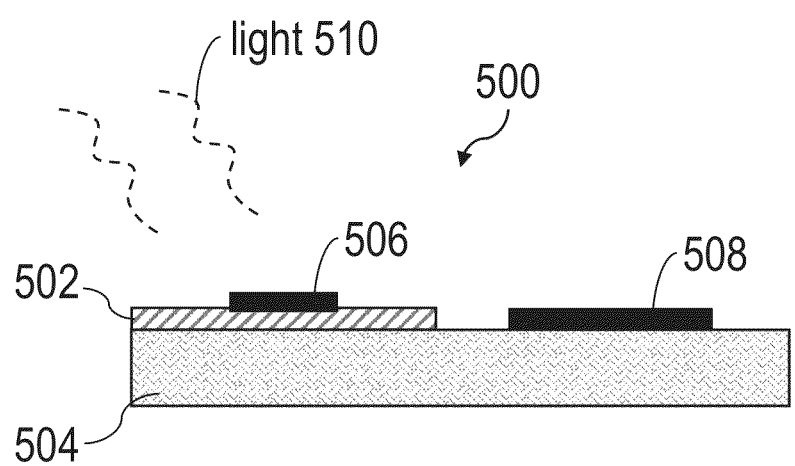
FIG. 5 is a diagram illustrating an example of a thin-film heterojunction photodetector.

In some implementations, the photodetectors are "self-powered" photodetectors that use thin-film heterojunctions to generate photocurrent. For example, as shown in FIG. 5, a photodetector 500 (which can be used, for example, as a photodetector 102 described above) includes a thin film of a first material 502 in contact with a second material 504. Respective conducting contacts 506, 508 are provided to carry signals to/from the first and second materials 502, 504. For example, the contacts 506, 508 can be metal contacts.

The first material 502 and the second material 504 are different from one another, such that a heterojunction is formed at the interface between the first and second materials 502, 504. For certain combinations of the first and second materials 502, 504, when the light 510 is incident on the first material 502 and/or the second material 504, substantial photocurrent is generated even in the absence of an external voltage applied to the photodetector 500. The combination of one or both of (i) a built-in electric field at the interface, or (ii) conduction band and/or valence band (or high occupied molecular orbital and/or lowest unoccupied molecular orbital) offsets at the interface, can provide for photodetection with high photoresponsivity, fast response rate, low dark current, and high light on/off ratio. In some cases, other or additional mechanisms can provide for these parameters. Some or all of these parameters can be higher in thin-film heterojunction devices, in a self-powered mode in the absence of active bias, than in homojunction devices, such as conventional silicon pn junctions.

Various combinations of morphologies and material types for the first material 502 and the second material 504 are within the scope of this disclosure. In some implementations, one or both of the first material 502 or the second material 504 is a two-dimensional material, such as a monolayer or otherwise ultrathin layer of graphene, black phosphorous (BP), a transition metal dichalcogenide (TMD, such as tungsten disulfide ($WS_2$), molybdenum disulfide ($MoS_2$), or platinum ditelluride ($PtTe_2$)), or another material, such as gallium selenide (GaSe) or indium selenide (InSe). Suitable two-dimensional materials, despite their thin depth, interact strongly with light and, moreover, are naturally passivated, lacking dangling bonds at their interfaces. These properties of two-dimensional materials can make them effective for inclusion in passive eye implants.

In some implementations, the first material 502 is a thin film, and the second material 504 is a bulk materials, such as a substrate on which thin film is disposed. For example, the second material 504 can be a silicon substrate, and the first material 502 can be a two-dimensional material, such as graphene. In some implementations, both the first material 502 and the second material 504 are two-dimensional materials, e.g., two of the types of two-dimensional materials indicated above, or another type of two-dimensional material. In some implementations, in a Schottky-type self-powered photodetector, one of the first material 502 or the second material 504 is a metal (such as nickel, platinum, gold, or another metal) and the other is a semiconductor or a two-dimensional material. When the first material 502 or the second material 504 is a metal, a contact 506, 508 need not be included to contact the metal, because the metal serves as its own contact.

Accordingly, passive photodetectors and passive circuitry produce signals that stimulate neurons via electrodes. Although the passive design of the eye implants described herein can, in some implementations, limit a complexity of processing performed on the signals, the human nervous system is highly adaptable and flexible. Over an extended period of use, the human nervous system will adapt to the signals that are provided by the electrodes, processing the signals in a manner necessary to provide obtain useful optical information and provide visual information to the user of the eye implant.

While this specification contains many specifics, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Moreover, the separation of various system components in the embodiments described above should not be understood as requiring such separation in all embodiments.

Other embodiments fall within the scope of the following claims.

What is claimed is:

1. A retinal implant comprising:
a plurality of photodetectors;
a plurality of electrodes electrically coupled to the plurality of photodetectors, the plurality of electrodes arranged in an electrode array; and
a passive circuitry electrically coupled to a first electrode of the plurality of electrodes, wherein the passive circuitry is configured to adjust a spectral characteristic of a signal sent from a first photodetector of the plurality of photodetectors, through the first electrode, and to the one or more neurons electrically coupled to the first electrode, the passive circuitry being electrically coupled between the first photodetector and the first electrode,
wherein the plurality of electrodes are configured to electrically couple each photodetector of the plurality of photodetectors to one or more neurons,
wherein the electrical coupling between each photodetector and the one or more neurons is entirely passive,
wherein the electrical coupling between each photodetector and the one or more neurons is free from digital signal processing, and
wherein the plurality of photodetectors comprises photodiodes.

2. The retinal implant of claim 1, wherein the plurality of electrodes are configured such that the one or more neurons electrically coupled to each photodetector are electrically disconnected from each other photodetector of the plurality of photodetectors.

3. The retinal implant of claim 1, wherein each photodetector of the photodetector array is electrically coupled to a corresponding electrode of the electrode array, and wherein the electrodes of the electrode array are arranged in an array pattern that matches an array pattern in which the photodetectors of the photodetector array are arranged.

4. The retinal implant of claim 1, wherein the passive circuitry comprises a frequency filter.

5. The retinal implant of claim 1, wherein the plurality of photodetectors comprise self-powered thin-film heterojunction photodetectors.

6. The retinal implant of claim 5, wherein the self-powered thin-film heterojunction photodetectors comprise a two-dimensional material.

7. The retinal implant of claim 1, wherein the plurality of electrodes each comprise a negative Poisson's ratio material.

8. The retinal implant of claim 7, wherein, for each electrode of the plurality of electrodes, the negative Poisson's ratio material of the electrode is coated by a positive Poisson's ratio material.

9. The retinal implant of claim 1, wherein the plurality of electrodes comprise a coating comprising at least one of a biocompatible polymer or a biocompatible ceramic.

10. The retinal implant of claim 1, wherein the plurality of electrodes each comprise an extending tip having a surface, wherein at least a portion of the surface is electrically conductive.

11. The retinal implant of claim 10, comprising a substrate having a first surface and a second surface opposite the first surface, wherein the plurality of photodetectors are disposed on the first surface, and wherein the extending tip of each electrode of the plurality of electrodes extends from the second surface away from the substrate.

* * * * *